United States Patent [19]

Haber et al.

[11] Patent Number: 5,275,613
[45] Date of Patent: Jan. 4, 1994

[54] ENDOSCOPIC TISSUE MANIPULATOR

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 850,674

[22] Filed: Mar. 13, 1992

Related U.S. Application Data

[63] Continuation-in-part of Ser. No. 839,510, Feb. 21, 1992.

[51] Int. Cl.$^5$ .............................................. A61B 17/00
[52] U.S. Cl. ................................. 606/205; 606/139; 606/144; 606/148; 606/207; 606/208
[58] Field of Search ..................... 606/205–; 81/385–

[56] References Cited

U.S. PATENT DOCUMENTS

| 1,274,669 | 8/1916 | Bohn | 606/206 |
|---|---|---|---|
| 2,363,334 | 11/1944 | Jones | 606/147 |
| 2,365,647 | 12/1944 | Ogburn | 606/147 |
| 3,168,097 | 2/1965 | Dormia | 606/147 |
| 3,895,636 | 7/1975 | Schmidt . | |
| 4,152,920 | 5/1979 | Green . | |
| 4,491,135 | 1/1985 | Klein . | |
| 4,562,839 | 1/1986 | Blake et al. | 606/143 |
| 4,580,567 | 4/1986 | Schweitzer et al. | 606/207 |
| 4,643,190 | 2/1987 | Heimberger . | |
| 4,706,668 | 11/1987 | Backer . | |
| 4,760,848 | 8/1988 | Hasson . | |
| 4,815,476 | 3/1989 | Clossick | 606/207 |
| 4,872,456 | 10/1989 | Hasson | 606/207 |
| 4,890,615 | 1/1990 | Caspari et al. | 606/146 |
| 4,898,157 | 2/1990 | Messroghli et al. . | |
| 4,935,027 | 6/1990 | Yoon . | |
| 4,944,093 | 7/1990 | Falk . | |
| 4,950,273 | 8/1990 | Briggs . | |
| 5,084,054 | 1/1992 | Bencini . | |
| 5,147,373 | 9/1992 | Ferzli . | |

FOREIGN PATENT DOCUMENTS 0586661 3/1947 United Kingdom .
2044108 10/1980 United Kingdom .

OTHER PUBLICATIONS

JARIT Laparoscopic Cholecystectomy Instruments, STAR 2000 Series, 1991.

Primary Examiner—Stephen C. Pellegrino
Assistant Examiner—Jeffrey A. Schmidt
Attorney, Agent, or Firm—Townsend and Townsend Khourie and Crew

[57] ABSTRACT

A instrument (2), particularly suited for endoscopic use, has an elongate body (4) including a base (6) and an elongate tip carrier tube (8) rotatably mounted to the base. A removable tip assembly (10), mounted at the distal end of the tip carrier tube, includes jaws (26,28) actuated by finger and thumb loops (16,18) mounted to the base. A rotary actuator trigger (78) is slidably mounted to the base. The tip carrier tube has a spiral groove (90) engaged by a cam pin (82) extending from the trigger so that axial movement of the trigger causes rotary motion of the tip carrier tube and the tip assembly therewith.

10 Claims, 15 Drawing Sheets

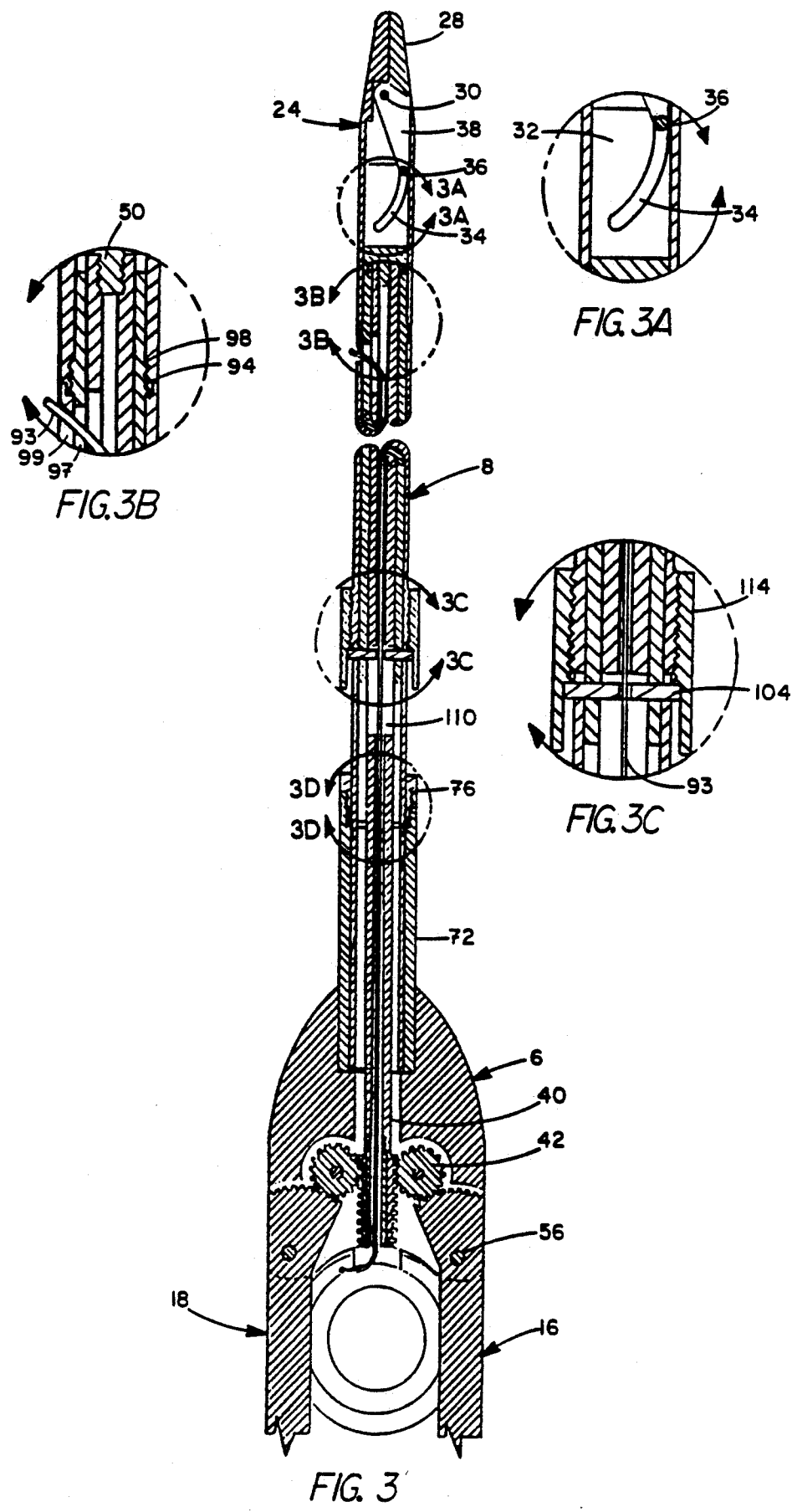

ENDOSCOPIC TISSUE MANIPULATOR

CROSS REFERENCE TO RELATED APPLICATION

This is a continuation-in-part of U.S. patent application Ser. No. 07/839,510 filed Feb. 21, 1992 for NEEDLE MANIPULATOR, the disclosure of which is incorporated by reference.

BACKGROUND OF THE INVENTION

Endoscopic surgery is widely used because it is much less traumatic than conventional open surgery. With endoscopic surgery, an incision is made in the patient's body and a port is passed through the incision. Various types of endoscopic instruments are passed through the port and appropriate procedures are carried out.

One type of endoscopic instrument is forceps having tips specially configured to grasp objects and cut tissue. Conventional forceps typically use scissors type of thumb and finger holes offset to one side of the axis in a pistol grip-type of arrangement. Such forceps, although well designed for cutting and simple grasping tasks, are not particularly suited for certain tasks, such as manipulating a needle during endoscopic procedures; conventional forceps require the user to reposition the entire instrument to adjust the rotary orientation of the tip.

SUMMARY OF THE INVENTION

The present invention is directed to an endoscopic surgical instrument which permits the user to independently actuate the tip and rotate the tip through manipulation of the handle assembly. This is accomplished without requiring the user to rotate his or her wrist.

The endoscopic surgical instrument includes broadly a tip assembly which is actuated by handle assembly. The tip assembly is preferably removable and replaceable. This allows a single instrument with a set of tip assemblies to be used to, for example, cut tissue, grasp tissue, dilate a region, manipulate a staple while closing an incision in tissue, hold a needle to suture tissue closed or tie a knot in suture material.

The endoscopic surgical instrument has an elongate body including a base and an elongate tip carrier rotatably mounted to the base. A, preferably removable, tip assembly is mounted at the distal end of the tip carrier. The removable tip assembly includes at least one movable jaw which is coupled to a pair of thumb and finger loops mounted to the proximal end of the body by an elongate drive assembly. The thumb and finger loops are preferably located on opposite sides of the axis of the elongate body. The thumb and finger loops move the drive assembly axially, such as through the engagement of gear teeth on the thumb and finger loops and on the drive rod or by the use of articulating linkage.

A rotary actuator trigger is preferably slidably mounted to the proximal end of the body. The tip carrier has, in the preferred embodiment, a spiral groove at a proximal end thereof. The spiral groove is engaged by a cam pin mounted to the rotary actuator trigger so that axial movement of the rotary actuator trigger causes rotary motion of the tip carrier and the tip assembly therewith.

When constructed as a needle manipulator, the user can clamp a suturing needle between the jaws and rotate the needle through one-handed manipulation: the jaws are opened and closed using one's thumb and middle finger while the jaws are rotated using one's index finger. A supply of suture material can be mounted to the trigger. The suture material can be directed up through the tip carrier, passed out through a side port in the tip carrier and supplied to the needle held by the jaws.

The invention provides several advantages over conventional grasping forceps. The jaw rotator assembly permits the user to rotate the tip assembly by pulling or pushing on the rotary actuator trigger. Incorporating the jaws or other operational tip elements as part of a removable tip assembly allows a single needle manipulator to be used with a number of tip assemblies to accommodate different specific types, sizes or shapes of needles and other objects. The jaw actuating thumb and finger loops are positioned so that they lie on opposite sides of the axis of the manipulator. This allows the user to rotate the needle manipulator by rotating one's wrist. In contrast, especially with the prior art pistol-type handles, rotation of the instrument about its axis is more difficult and less precise.

Other features and advantages of the invention will appear from the following description in which the preferred embodiments have been set forth in detail in conjunction with the accompanying drawings.

BRIEF DESCRIPTION OF THE DRAWINGS

FIG. 3 is a cross-sectional view of a portion of the needle manipulator of FIG. 1 with the jaws in a closed position;

FIGS. 3A-3D show portions of the needle manipulator of FIG. 3 enlarged to show detail;

DESCRIPTION OF THE PREFERRED EMBODIMENTS

Figure 1:
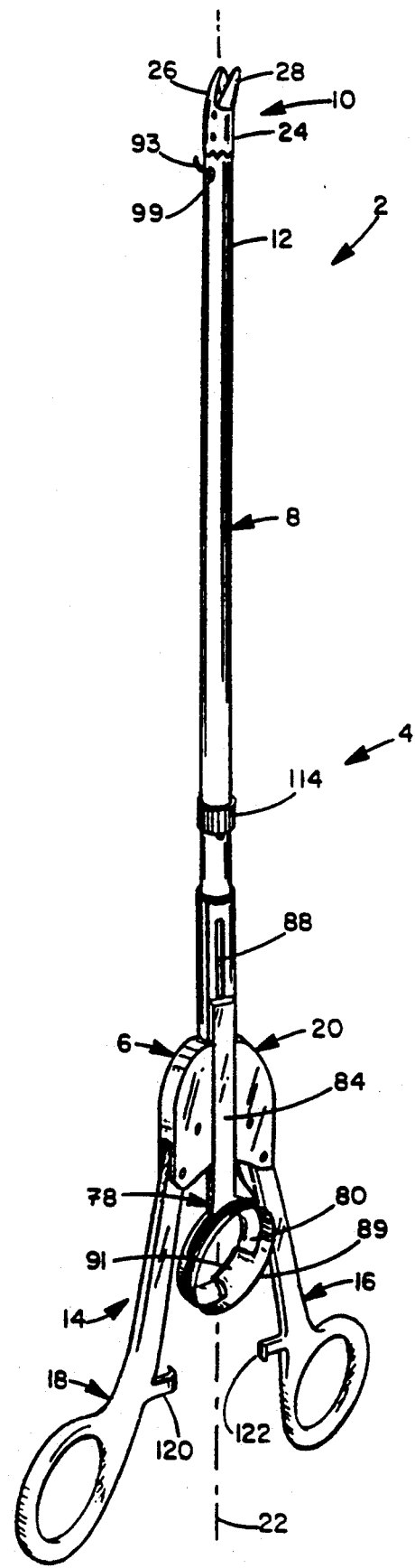
FIG. 1 is an overall perspective view of a needle manipulator type of endoscopic surgical instrument made according to the invention.

FIG. 1 illustrates a needle manipulator type of endoscopic surgical instrument made according to the invention. Needle manipulator 2 includes an elongate body 4, the body including a base 6 and an elongate tip carrier tube 8. Manipulator 2 also includes a tip assembly 10 mounted to the distal end 12 of tube 8 and a jaw driver assembly 14. Jaw driver assembly 14 is used to manipulate the jaws carried by the tip assembly as is described below through the opening and closing of jaw actuating finger and thumb loops 16, 18. Manipulator 2 further includes a jaw rotator assembly 20 used to rotate tip carrier tube 8 and tip assembly 10 therewith about the longitudinal axis 22 of the manipulator.

Figure 2:
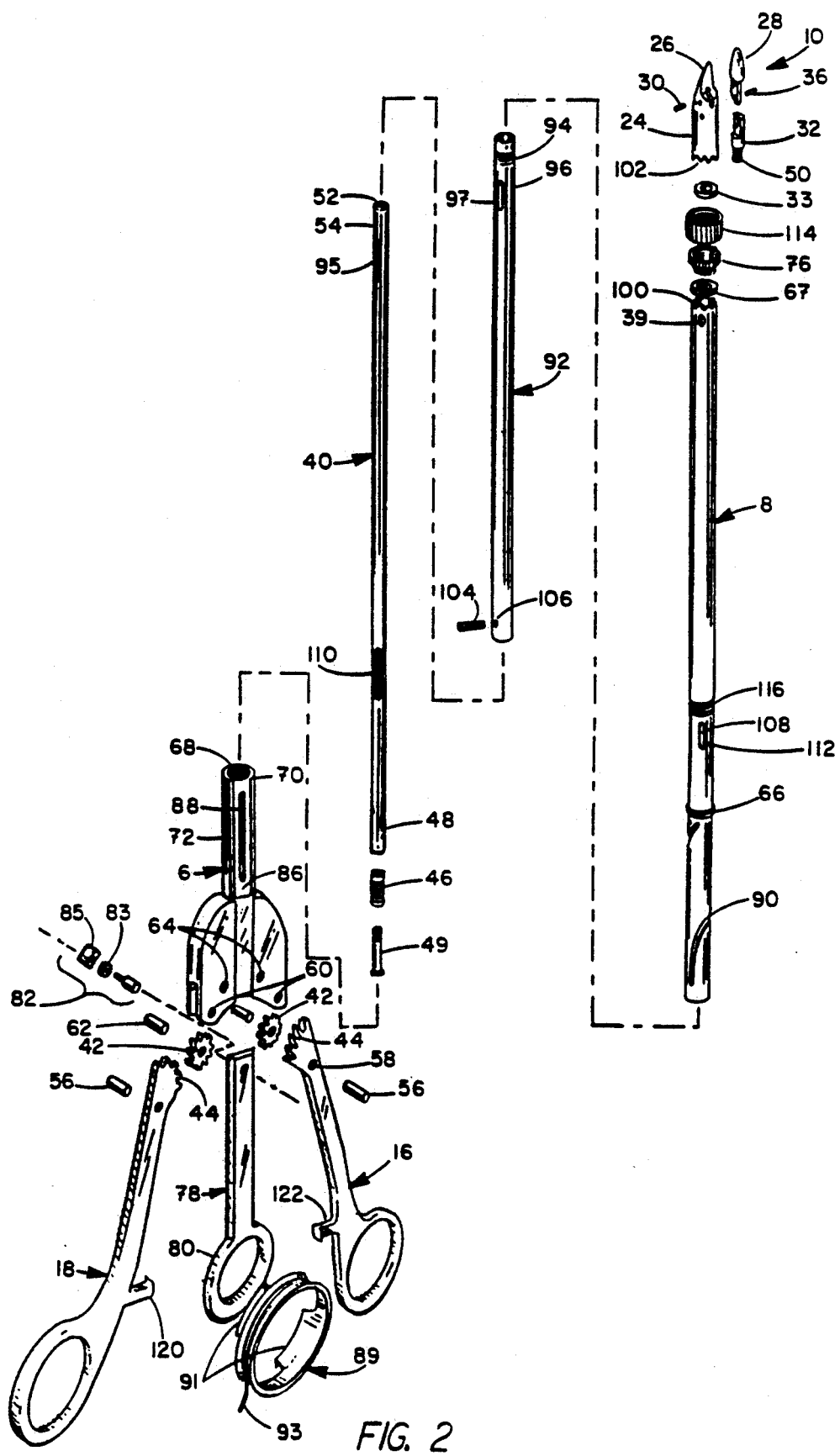
FIG. 2 is an exploded isometric view of the needle manipulator of FIG. 1.
Figure 3D:
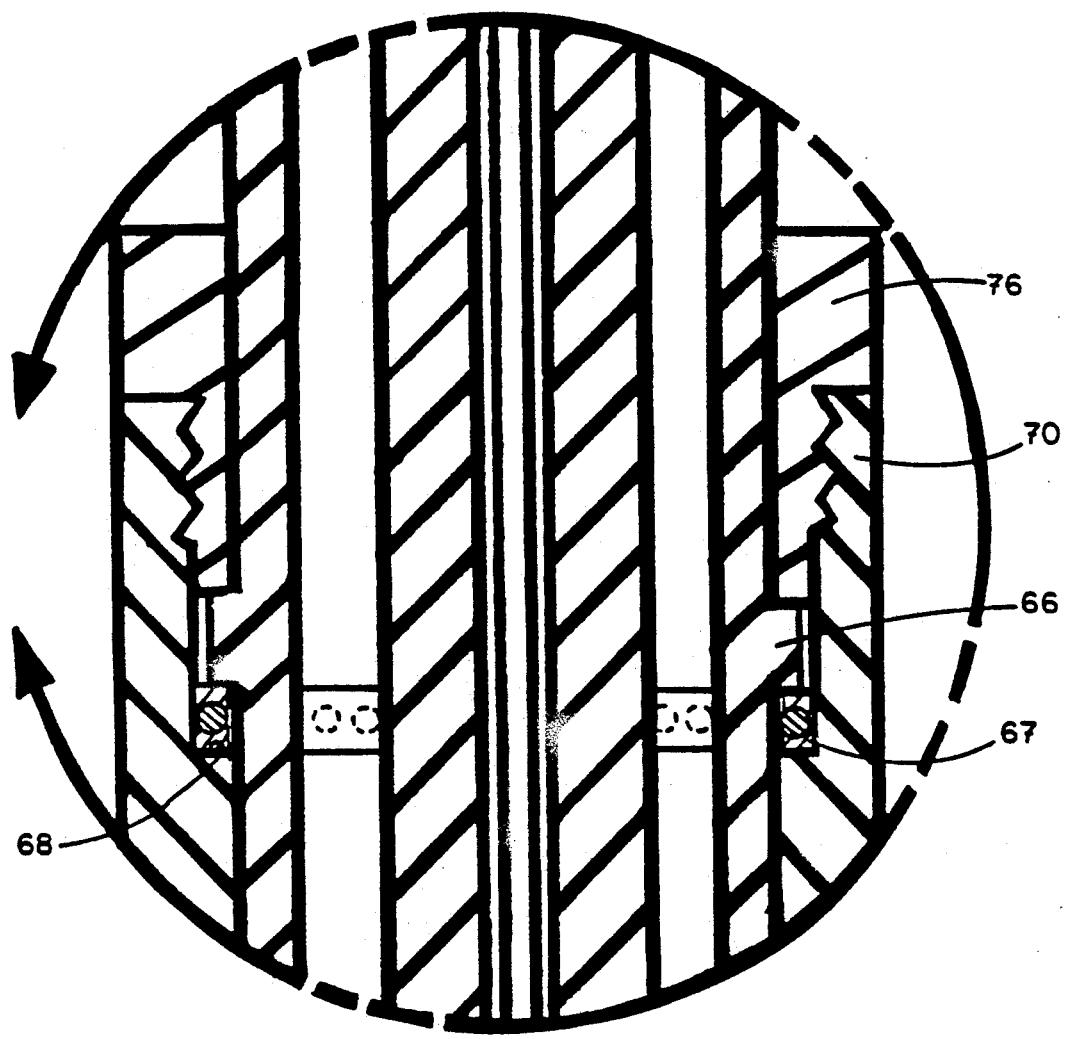
Figure 4:
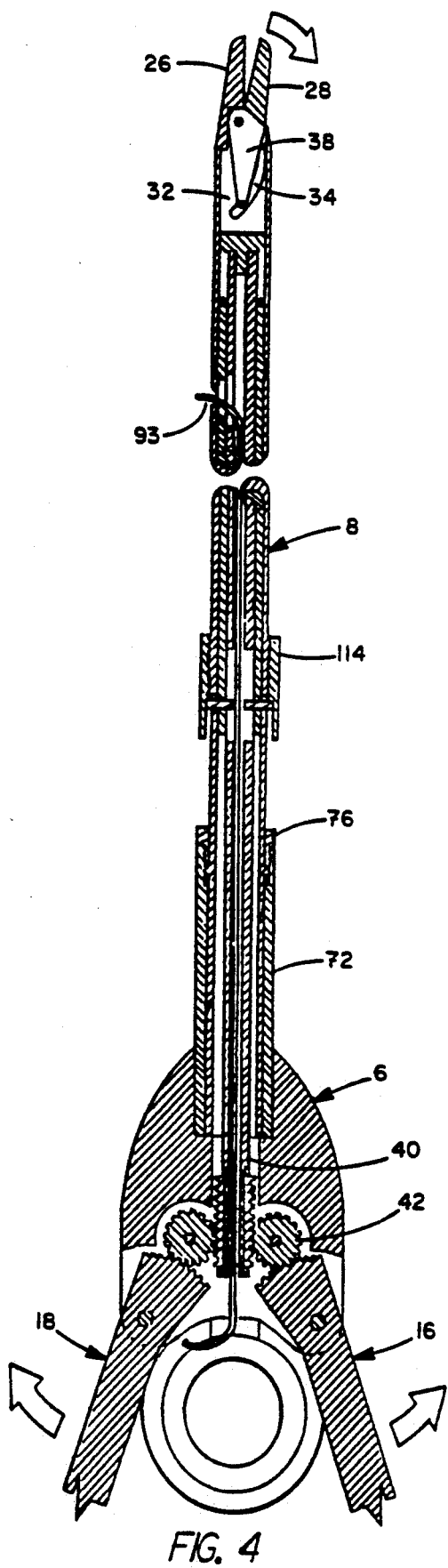
FIG. 4 shows the needle manipulator of FIG. 3 with the jaws in the open position.
Figure 5:
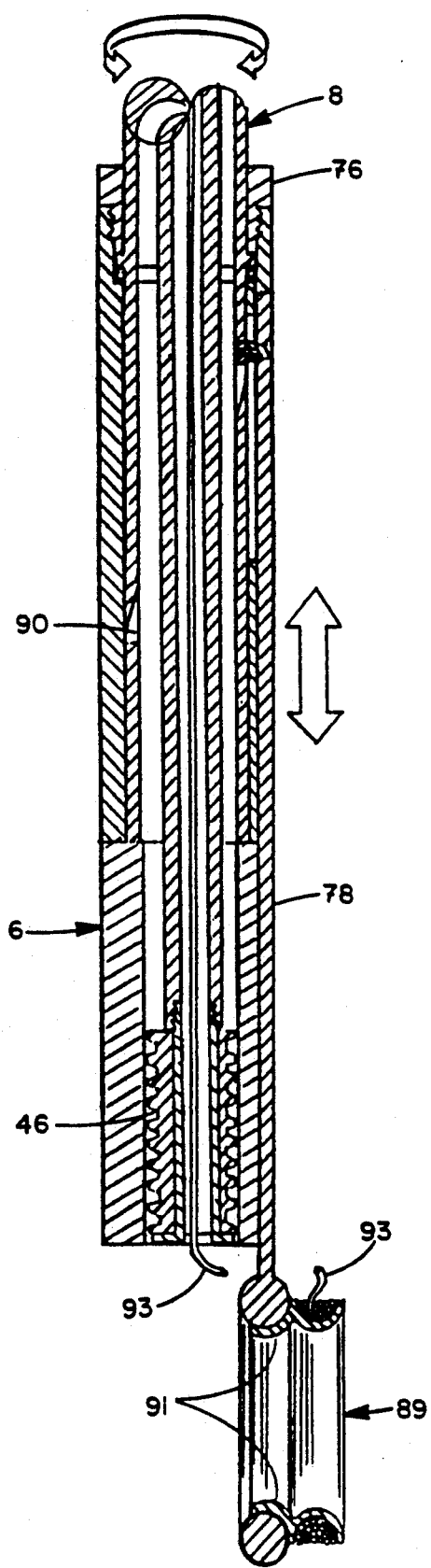
FIG. 5 is a cross sectional view of a portion of the needle manipulator of FIG. 1 taken in a plane perpendicular to the plane of FIG. 3.

FIG. 2 illustrates tip assembly 10 as including a tip 24 having a fixed jaw 26 integral with tip 24 and a movable jaw 28 secured to tip 24 by a pivot pin 30. Tip assembly 10 also includes an adapter 32 sized to fit within and slide within the hollow interior of tip assembly 10. Adapter is held within the interior of tip 24 by a ring 33 press fit into the tip interior. Adapter 32 has a cam slot 34 within which a drive pin 36 extending from an end 38 of movable jaw 28 rides. Thus, axial movement, that is movement parallel to axis 22, of adapter 32 causes movable jaw 28 to move from the closed jaw position of FIG. 3 to the open jaw position of FIG. 4. This is accomplished by the manipulation of jaw driver assembly 14. (See FIG. 1.)

Jaw driver assembly 14 includes finger and thumb loops 16, 18 coupled to an axial drive rod 40 through the engagement of idler gears 42 with drive gear segments 44 formed on finger and thumb loops 16, 18 and a rotary rack 46 formed on the proximal end of 48 of drive rod 40. Rack 46 is secured to end 48 by a screw 49 to permit rack 46 to rotate freely. Adapter 32 includes a threaded tip 50 which engages a threaded hole 52 at the distal end of 54 of rod 40. Finger and thumb loops 16, 18 are pivotally mounted to base 6 through the use of pivot pins 56 passing through pivot holes 58 formed in loops 16, 18 and pivot pin bores 60 formed in base 6. Idler gears 42 are secured to base 6 by idler gear pins 62 which pass through bores in the idler gears and through idler gear pin holes 64 in base 6.

Tip carrier tube 8 has an annular shoulder 66 sized and positioned to seat against a thrust bearing 67 supported by an internal annular surface 68 formed at the distal end 70 of barrel portion 72 of base 6. See FIG. 3D. The proximal end 74 of tube 8 is maintained within base 6 by an externally threaded ring 76. Ring 76 is sized so that when the ring is secured against distal end 70 of barrel portion 72, tube 8 is securely mounted to base 6 but is free to rotate within the base. Thrust bearing 67 helps to ensure the free rotation of tube 8 during use.

Jaw rotator assembly 20 includes a rotary actuator trigger 78 having a finger loop 80 at its proximal end and a cam pin 82 at its distal end. Trigger 78 includes elongate portion 84 having a dovetail or trapezoidal cross-sectional shape which slides within a similarly configured dovetail slot 86 formed along the length of base 6. Pin 82 passes through an axial slot 88 formed in barrel portion 72 along slot 86. Pin 82 passes through slot 88 to engage a spiral groove 90 formed in proximal end 74 of tube 8. Pin 82 includes a ring 83 which rides within slot 88 and a guide 85 which rides within spiral groove 90, both ring 83 and guide 85 preferably made of PTFE. Thus, axial movement of trigger 78 causes pin 82 to ride along spiral groove 90, thus rotating tube 8 and tip assembly 10 therewith about axis 22.

Tip assembly 10 is secured to tip carrier tube 8 using a hollow tip mounting tube 92. Tip mounting tube 92 has external threads 94 at its distal end 96 which engage internal threads 98 formed within the interior of tip 24. Tip 24 and tip carrier tube 8 have opposed, complementary tooth surfaces 100, 102 which, when engaged, keep tip assembly 10 from rotating relative to tip carrier tube 8. Tube 8, mounting tube 92 and drive rod 40 are secured to one another by a common pin 104. Pin 104 passes through a bore 106 in mounting tube 92, a short slot 108 in carrier tube 8 and a long slot 110 in drive rod 40. Common pin 104 is maintained at the proximal end 112 of slot 108, thus keeping tooth surfaces 102, 100 engaged, through the use of an internally threaded ring 114 threaded onto external threads 116 formed on the outside of tube 8 adjacent slot 108. Slot 110, being longer than slot 108, can still move axially through the manipulation of finger and thumb loops 16, 18, thus causing jaws 26, 28 to open and close.

A suture material supply spool 89 is mounted to finger loop 80 through the use of snap flanges 91 which engage the inside of the finger loop. Suture material 93 is directed from needle 118, through hole 99 in tube 8, through slots 95, 97 in rod 40 and tube 92, through the center of rod 40 and is wound about spool 89.

The operation of needle manipulator 2 will now be described. The user places his or her thumb and middle finger through thumb and finger loops 18, 16. Loops 18, 16 are separated, as suggested in FIG. 4, causing drive gear segments 44 to rotate idler gears 42 which, in turn, drive rotary rack 46 axially, that is parallel to axis 22. This causes adapter 32 to move axially so that drive pin 36 moves along cam slot 34, thus opening jaws 26, 28 through the pivotal movement of movable jaw 28. A needle 118 is placed between jaws 26, 28 and is secured in place by moving finger loops 16, 18 back towards one another to the position of FIGS. 1 and 3. Needle 118 is locked between jaws 26, 28 through the engagement of catches 120, 122 carried by loops 16, 18. The manipulation of rotary actuator trigger 78 parallel to axis 22 causes pin 82 to ride along spiral groove 90, thus rotating tip carrier tube 8 and tip assembly 10 therewith about axis 22. Tip mounting tube 92 and axial drive rod 40 are likewise rotated about axis 22 upon the actuation of trigger 78 due to the interlocking engagement of common pin 104 with all three members. With needle manipulator 2, the user's hand, wrist and arm can be generally aligned with axis 22 for enhanced control.

Figure 6:
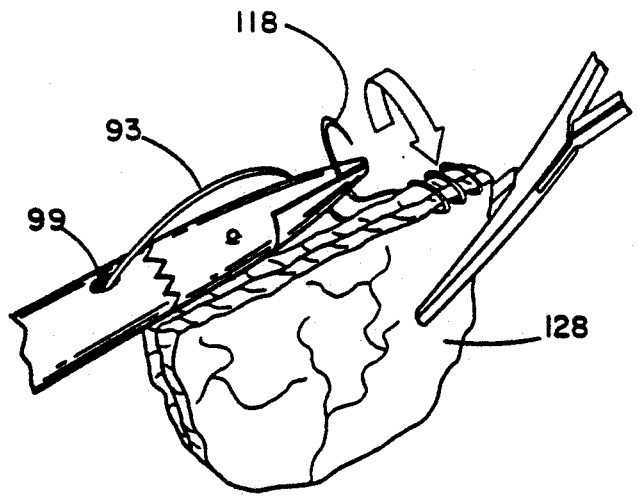
FIG. 6 is an enlarged view of the tip assembly of FIG. 1 shown manipulating a needle to suture tissue.
Figure 6A:
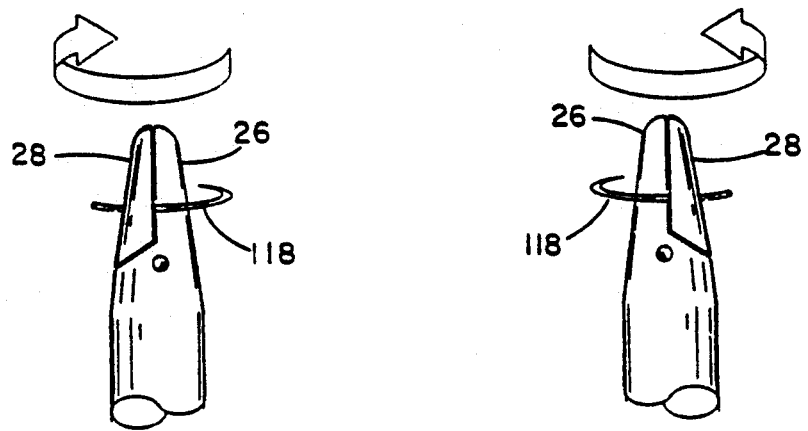
FIGS. 6A and 6B illustrate the rotary movement of the tip assembly and needle of FIG. 6 as the trigger is pulled and pushed, respectively.
Figure 6A:
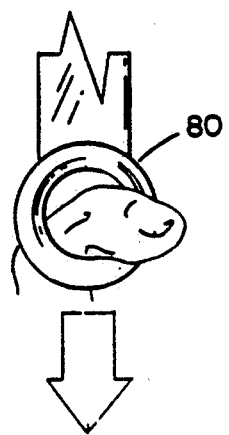
Figure 6B:
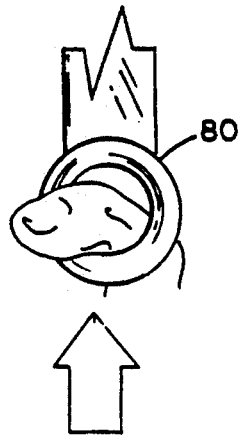
Figure 7:
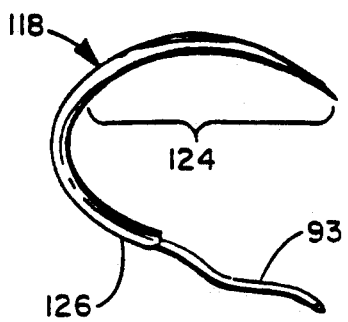
FIGS. 7 and 7A are enlarged plan and side views of the needle of FIG. 6 showing the attachment of the suture material and the special shape of the needle.
Figure 7A:
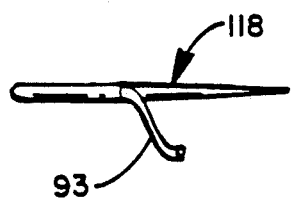
Figure 7B:
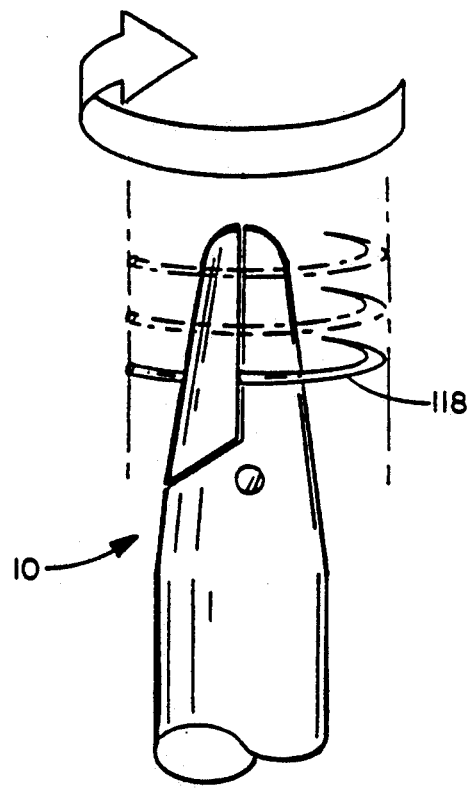
FIG. 7B illustrates the progression of the needle of FIG. 6 after successive stitches caused by rotation of the tip assembly and needle.
Figure 8A:
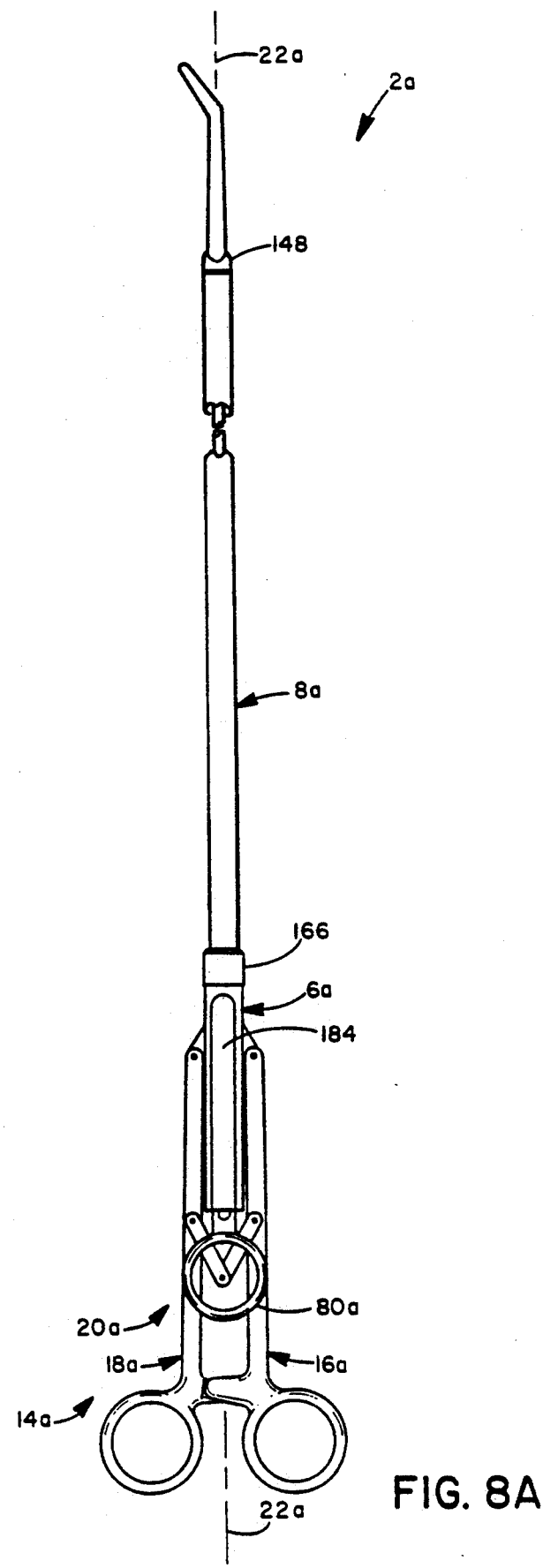
FIGS. 8A, 8B and 8C are side views of a grasping type of endoscopic medical instrument made according to the invention shown in a closed jaw position in FIG. 8A, an open-jaw position in FIG. 8B with the tip assembly rotated 90° from the position of FIG. 8A, and a closed jaw position in FIG. 8C with the tip assembly rotated 180° from the position of FIG. 8A.
Figure 8B:
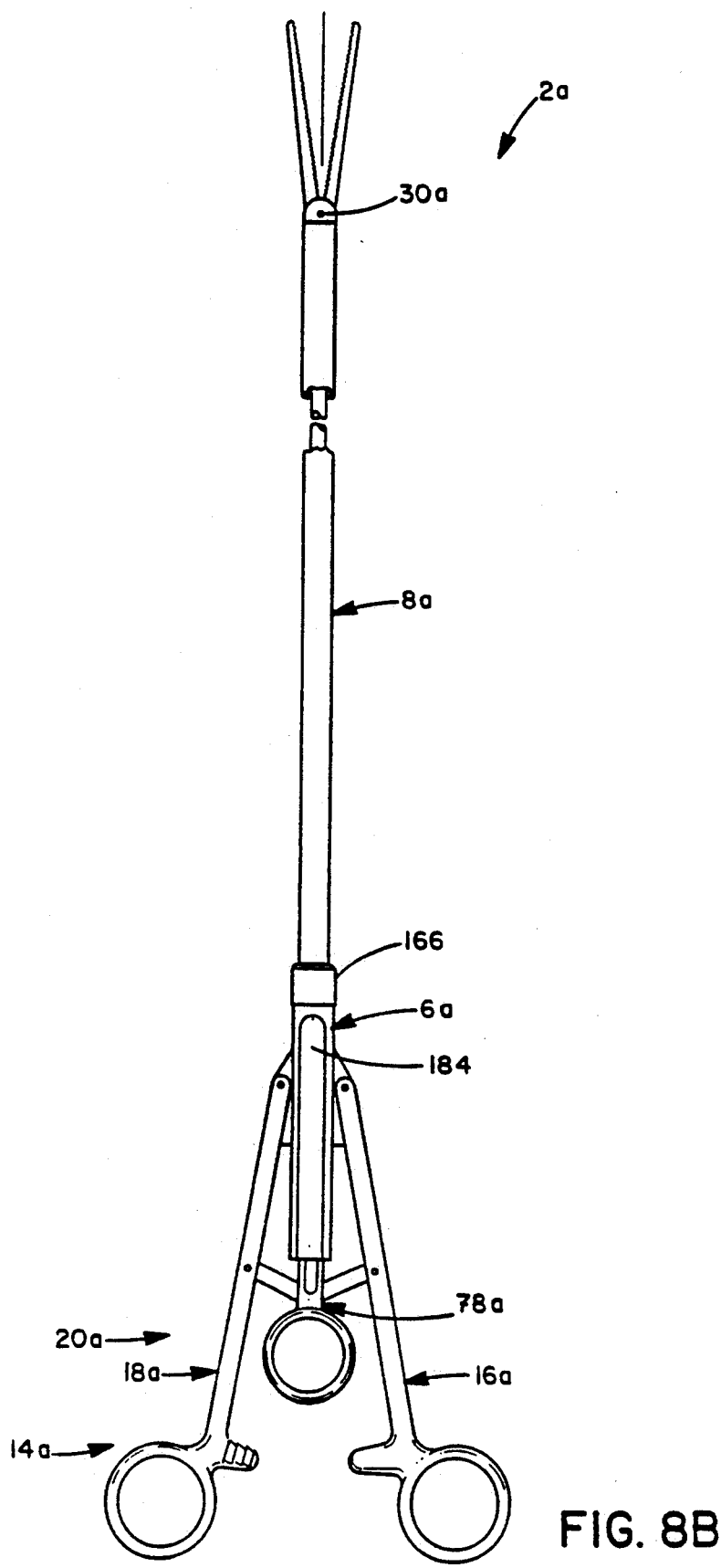
Figure 8C:
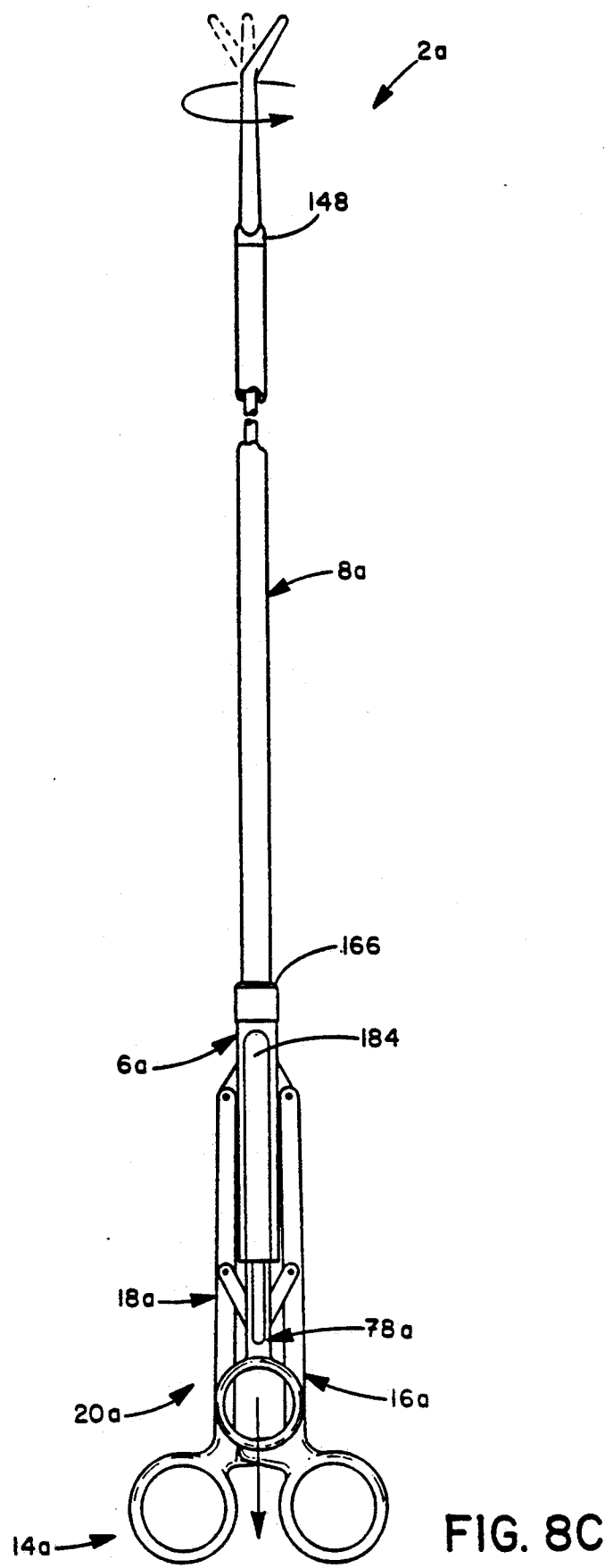

The reciprocal movement of trigger 78 causes tip assembly 10 and needle 93 to move in opposite rotary directions. See FIGS. 6, 6A and 6B. In the preferred embodiment this movement is through an arc of about 240°. Only when needle 93 is moved in the appropriate rotary direction, clockwise in FIG. 6, will the needle pierce tissue 128. After the piercing movement, the user releases needle 118 from between jaws 26, 28, rotates tip assembly 10 in the opposite direction, regrasps needle 118 between jaws 26, 28, pulls needle 118 completely through tissue 128, repositions needle 118 between jaws 26, 28 at a position 126 along the needle and repeats the process.

Needle 118 has a generally elliptical shape with a main portion 124 having a generally circular shape. Needle 118 can be grasped between jaws 26, 28 at a position 126 adjacent the attachment point for suture material. Point 126 is located at about the center of the generally circular arc formed by a main portion 124 so that when tip assembly 10 is rotated about axis 22, main portion 124 moves along a generally circular path. This minimizes trauma to tissue 128 and makes the procedure easier to perform.

Turning now to FIGS. 8-10B, an alternative embodiment of the endoscopic medical instrument of FIGS. 1-7B is shown. Parts of the alternative embodiment which correspond to the embodiment of FIG. 1 have like reference numerals. The alternative embodiment is an endoscopic medical instrument of the grasping type having a pair of movable jaws 28a, 28b as part of the tip assembly 10a. Instrument 2a includes broadly an elongate body 4a, a tip assembly 10a removably mounted to the distal end 12a of a tip carrier tube 8a, a driver assembly 14a, which causes jaws 28a, 28b to move between their open and closed positions, and a jaw rotator assembly 20a, which causes tip assembly 10a, and jaws 28a, 28b therewith, to rotate about axis 22a.

Jaws 28a, 28b include outer portions 140 and arm portions 142 connected by hubs 144 having holes 146 formed therein. Tip assembly 10a also includes a circular, hollow tip coupler plug 148 having a through hole 150 formed perpendicular to axis 22a. Jaws 28a, 28b are mounted within tip coupler plug 148 and are pivotally secured within the plug by pivot pin 30a. The interior of tip coupler plug 148 is sized to permit jaws 28a, 28b to move between their open and closed positions of FIGS. 8A and 8B.

Figure 10A:
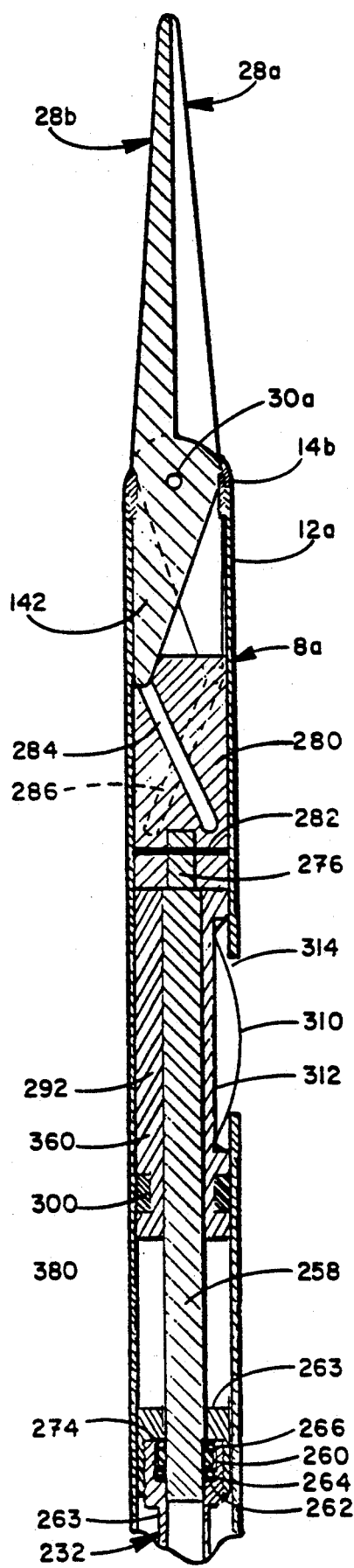
FIGS. 10A and 10B are longitudinal cross sectional views of the distal and proximal portions of the instrument of FIGS. 9A and 9B.
Figure 10B:
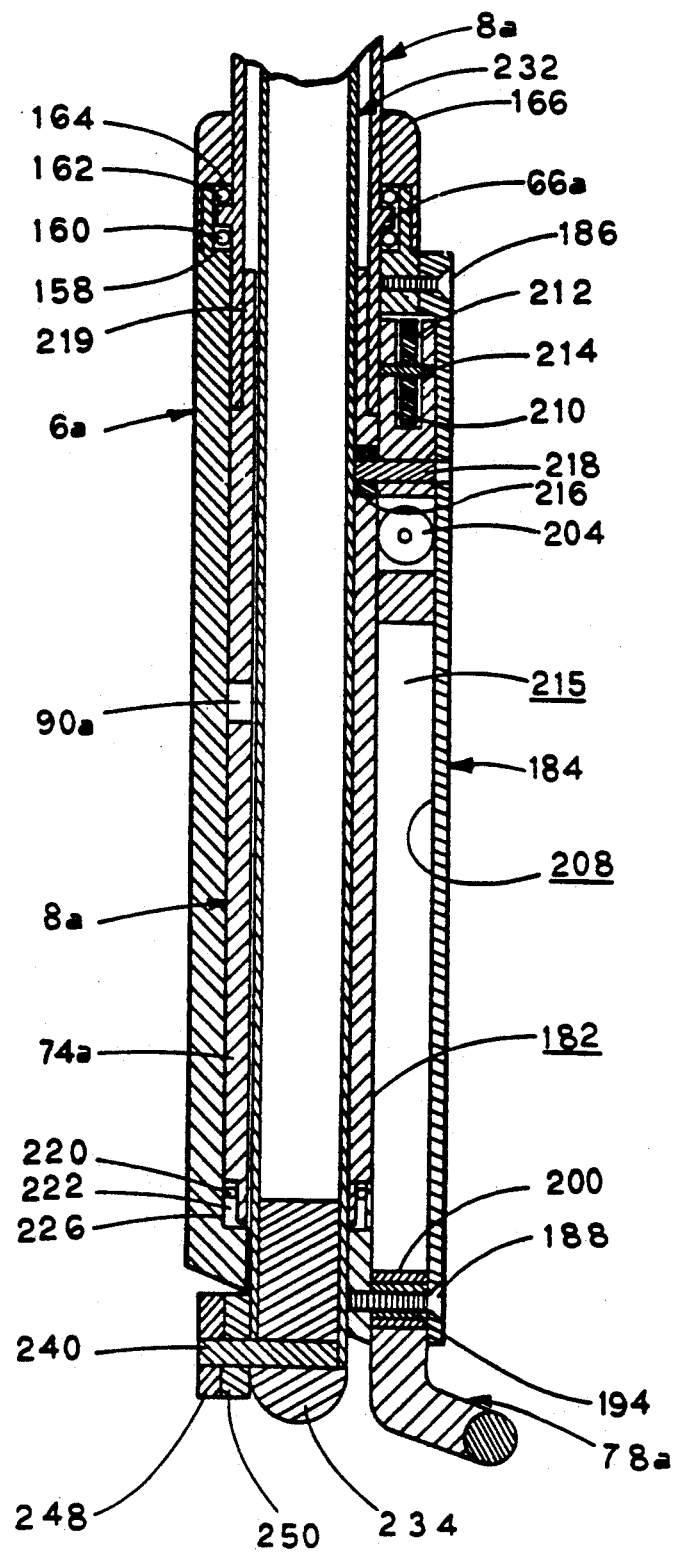

Tip coupler plug 148 has external threads 152 formed on one end. Threads 152 are sized to engage internal threads 154 formed at distal end 12a of tip carrier tube 8a. In this way, tip assembly 10a can be removably secured to body 4a of instrument 2a. Tip carrier tube 8a is sized so that proximal end 74a fits within the hollow interior 156 of base 6a. Base 6a, as shown in FIG. 10B, has an inner shoulder 158 which supports annular shoulder 66a of tip carrier tube 8a. A set of ball bearings 160 is positioned between shoulder 66a and shoulder 158. Another set of ball bearings 162 is situated between annular shoulder 66a and an inner shoulder 164 of a tip carrier tube retaining nut 166. Nut 166 has a threaded interior 168 which engages the threaded exterior 170 of base 6a. Shoulders 158, 164 are positioned so that tip carrier tube 8a is secured axially to base 6a but is allowed relatively free rotary movement with respect to the base by virtue of ball bearing sets 160, 162.

Finger and thumb loops 16a, 18a are pivotally mounted to lugs 172 of base 6a using pins 174 which pass through openings 176 formed in the clevis ends 178 of loops 16a, 18a and corresponding holes 180 formed in lugs 172. Manipulation of loops 16a, 18a is used to open and close jaws 28a, 28b and will be discussed below.

Base 8a has flat face 182 extending substantially along its entire length. A hollowed out cover 184 is secured to base 6a by a pair of screws 186, 188. Screw 186 threads into a hole 190 in base 6a adjacent the distal end of flat face 182. Screw 188 passes through the hollow interior 192 of a standoff 194 and engages a threaded hole 196 formed in flat face 182 at the proximal end of axial slot 88a. A roller 200 is sized to be mounted over and rotate freely about standoff 94. Roller 200 is sized to fit within a slot 202 formed in trigger 78a and helps to stabilize trigger 78a as the trigger moves parallel to axis 22a. The stability of trigger 78a is also aided by the use of a pair of rollers 204 on either side of trigger 78a at the distal end 206 of the trigger. Rollers 204 ride between surface 182 and the overlying surface 208, as seen in FIG. 10B, of cover 184. Side to side movement of distal end 206 of trigger 78a is restricted by engagement of a roller 210 mounted in a slot 212 at distal end 206 of trigger 78a by a pin 214. Roller 210 is sized to ride along the side surfaces 215 of the hollow interior of cover 184.

Trigger 78a also includes a cam pin 82a. Cam pin 82a includes a cam roller 216 secured to distal end 206 by a pin 218. Cam pin 82a is positioned to extend through axial slot 88a and engage spiral groove 90a at proximal end 74a of tip carrier tube 8a. Thus, axial movement of trigger 78a causes cam pin 82a to move along spiral groove 90a, thus rotating tip carrier tube 8a and tip assembly 10a therewith about axis 22a.

FIG. 10B shows that proximal end 74a is thicker than the remainder of base 8a. This is to provide a deeper spiral groove 90a and thus a better camming surface for cam roller 216 to ride against. This dual wall thickness is achieved by overlapping tubes having different wall thicknesses as shown at overlapping region 219.

Lateral support of proximal end 74a within base 6a is aided by the use of a set of ball bearings 220 housed within an annular cavity 222. Cavity 222 is defined between the tip 224 of end 74a and a cupped shaped region 226 formed within base 6a adjacent proximal end 198.

Figure 9A:
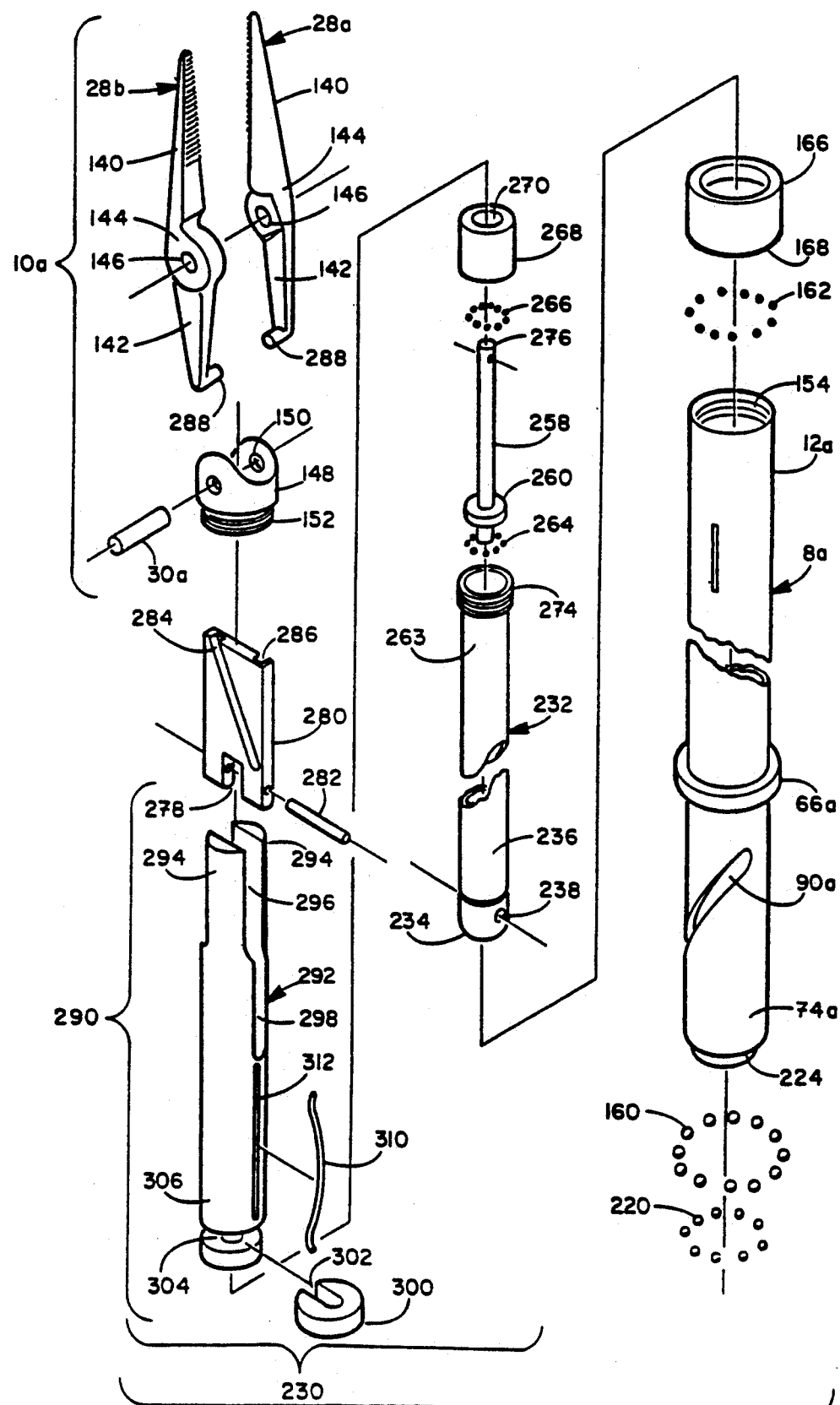
FIGS. 9A and 9B are exploded isometric views of the distal and proximal portions of the instrument of FIG. 8 shown with straight rather than doglegged jaws.
Figure 9B:
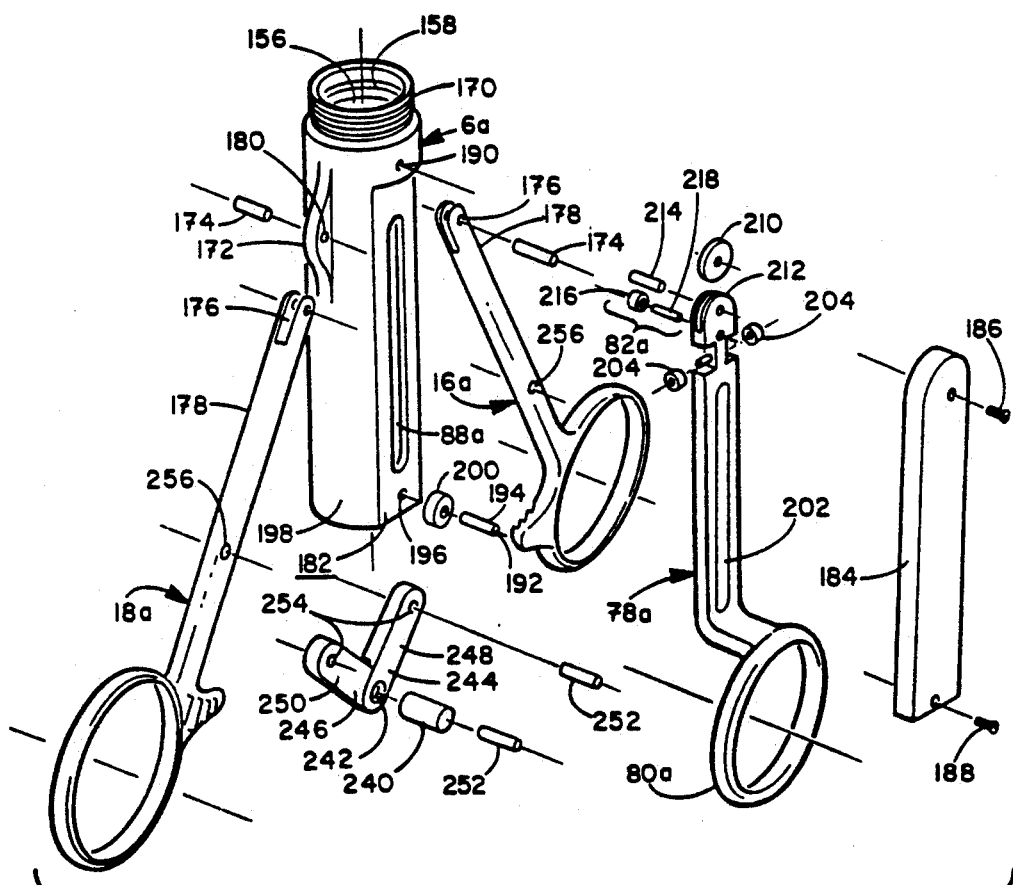

The remainder of jaw driver assembly 14a, in addition to finger and thumb loops 16a, 18a, will now be discussed. As shown in FIG. 9A, an axial drive tube assembly 230 includes an axial drive tube 232 having a plug 234 at a proximal end 236. Plug 234 has a transverse bore 238 through which a common pin 240 passes. Pin 240 also passes through aligned bores 242 formed in the overlapping ends 244, 246 of links 248, 250. Links 248, 250 are pivotally connected to finger and thumb loops 16a, 18a by pins 252 passing through holes 254, 256 formed in links 248, 250 and loops 16a, 18a. Thus, movement of finger and thumb loops 16a, 18a towards and away from each other causes links 248, 250 to articulate, thus driving axial drive tube 232 along axis 22a.

Axial drive tube assembly 230 also includes a flanged draw bar 258 with a flange 260 at a proximal end thereof. Flange 260 is sized to lie adjacent an internal shoulder 262 formed at the distal end 263 of tube 232 with a set of ball bearings 264 captured therebetween. A second set of ball bearings 266 is positioned on the other side of flange 260. A draw bar retaining nut 268 has a central bore 270 sized to fit over flanged draw bar 258. Nut 268 has an internal shoulder 272 which rests against the lip 274 of tube 232 to capture ball bearings 266 between nut 268, bar 258 and tube 232. Flanged draw bar 258 is thus fixed axially to axial drive tube 232 but is allowed to freely rotate within the axial drive tube.

The distal end 276 of bar 258 fits within a cut-out region 278 formed in a flattened rectangular cam block 280. Cam block 280 is secured to distal end 276 by a pin 282 passing through both. Cam block 280 has a pair of slots 284, 286 formed on either side of cam block 280 and angled in opposite directions. Arms 142 of jaws 28a, 28b each have inwardly extending pins 288 sized to engage slots 284, 286. Thus, axial movement of axial drive tube 232, which also moves flanged draw bar 258 and cam block 280 therewith, causes cam block 280 to move parallel to axis 22a thus causing pins 288 to slide along slots 284, 286; this causes jaws 28a, 28b to open and close in a grasping action.

Axial drive tube assembly 230 also includes a fork assembly 290 for stabilizing cam block 280 during use. Fork assembly 290 includes a fork 292 having a pair of arms 294 defining wider and narrower gaps 296, 298 therebetween. Wider gap 296 is sized to encompass arms 142 of movable jaws 28a, 28b while narrower gap 298 is sized to lie along either side and guide cam block 280.

Fork assembly 290 also includes a U-collar 300 having a slot 302 formed therein. Slot 302 is sized to fit loosely within an annular groove 304 formed at the proximal end 306 of fork 292. The outer circumference of U-collar 300 is sized to create a relatively tight friction fit within the interior 308 of tip carrier tube 8a. Thus, fork assembly 290 is fixed axially within tip carrier tube 8a while flanged draw bar 258 moves axially with fork 292.

Fork assembly 290 also includes a spring 310 partially housed within a fork spring slot 312 formed in fork 292 between groove 304 and narrower gap 298. Spring 310 is sized and positioned to engage a tube spring slot 314 formed in tip carrier tube 8a. In this way, fork assembly 290 is kept from rotating axially within tip carrier tube 8a. However, when first mounting tip assembly 10a to distal end 12a of tip carrier tube 8a, the user can depress spring 310 and allow fork assembly 290 to rotate along with cam block 280, tip assembly 10a and flange draw bar 258 until tip coupler plug 148 is screwed fully onto threads 154 of tip carrier tube 8a. At this point, spring 310 is allowed to freely enter slot 314 to prevent fork assembly 292 from rotating within tip carrier tube 8a. Thus, fork assembly 290 is used for two primary purposes: to guide and stabilize cam block 280 and arms 242 of jaws 28a, 28b and to keep tip assembly 10a from unscrewing from tip carrier tube 8a.

In use, assuming tip assembly 10a must be changed, spring 310 is depressed through slot 314 and tip assembly 10a is unscrewed from internal threads 154 at distal end 12a of tip carrier tube 8a. An appropriate tip assembly is then threaded onto distal end 12a. Using tip assembly 10a, pins 288 are guided into slots 284, 286 to permit both jaws 28a, 28b to move. In appropriate cases, a different cam block 280 could be used to accommodate a different type of motion; also, the tip assembly could be constructed so that only one jaw moves. Tip assembly 10a is rotated about axis 22a by the manipulation of trigger 78a. The axial movement of trigger 78a causes tip carrier tube 8a and tip assembly 10a secured thereto to rotate about axis 22a. Once properly oriented, the user opens and shuts jaws 28a, 28b by opening and closing finger and thumb loops 16a, 18a. Doing so articulates links 248, 250 which are coupled to axial drive tube 232 through common pin 240 and plug 234. Axial movement of drive tube 232 causes like axial movement of drawbar 258 which, being pinned to cam block 280 by pin 282, moves the cam block axially along axis 22a. The axial movement of cam block 280 causes transverse pivotal movement of jaws 28a, 28b as pins 288 ride along sots 284, 286 to provide the desired grasping action.

The invention has been shown in two different embodiments, one specially adapted as an endoscopic needle manipulator while the other as an endoscopic tissue grasper or manipulator. The invention can also be practiced using tips and tip assemblies configured for other uses. For example, tip assemblies adapted for dilating a region, cutting tissue, stapling tissue or knotting suture material could be used as well.

Modification and variation can be made to the disclosed embodiments without departing from the subject of the invention as defined in the following claims. For example, other methods for mounting tip assembly to the remainder of the device could be used as well. It may be desired to spring bias loops 16, 18 away from one another and trigger 78 towards the position of FIG. 1.

What is claimed is:

1. An endoscopic tissue manipulator comprising:
   a longitudinal body having a distal end and a proximal end;
   a tip assembly mounted to the distal end of the body, the tip assembly including a movable first jaw and a second jaw fixed to the body;
   a tip element driver assembly including a user manipulatable tip element actuator, movably mounted to the proximal end of the body, and having jaw actuating finger and thumb loops pivotally mounted on opposite sides of the longitudinal body, and an axial driver assembly coupling the tip element actuator to at least said movable first jaw, so that when the user manipulates the tip element actuator said moveable first jaw moves relative to the body and said second jaw; and
   a tip assembly rotator including a user manipulatable rotary actuator located between said jaw actuating finger and thumb loops and a rotary driver, drivingly axially coupling the rotary actuator ad the tip assembly, so that user axial manipulation of the rotary actuator causes the tip assembly to rotate about the longitudinal axis of said longitudinal body.

2. The manipulator of claim 1 wherein the axial driver assembly includes drive linkage segments and an axial drive tube having a proximal end coupled to the drive linkage segments.

3. The manipulator of claim 2 wherein the axial driver assembly includes a cam member secured to the drive tube for axial movement therewith, the cam member including a cam slot, the movable tip element engaging the cam slot so that axial movement of the cam member causes the tip element to move laterally.

4. The manipulator of claim 1 wherein the tip assembly is removably mounted to the body.

5. An endoscopic tissue manipulator comprising:
   a longitudinal body having a distal end and a proximal end;
   a tip assembly removably mounted to the distal end of the body;
   the tip assembly including at least one tip element, the tip element being movable relative to the body;
   a tip element driver assembly including a user manipulatable tip element actuator, movably mounted to the proximal end of the body, and an axial driver assembly coupling the tip element actuator to at least the tip element, so that when the user manipulates the tip element actuator the tip element moves relative to the body;
   the tip element actuator including tip element actuating finger and thumb elements movably mounted to the body, the body defining an axis passing through the distal and proximal ends, the finger and thumb elements being positioned on opposite sides of the axis; and
   a tip assembly rotator including a user manipulatable rotary actuator, movably mounted to the proximal end of the body, between said finger and thumb elements and a rotary driver, drivingly axially coupling the rotary actuator and the tip assembly, so that user axial manipulation of the rotary actuator causes the tip assembly to rotate about the axis.

6. An endoscopic surgical instrument comprising:

a body having a tip carrier tube at a distal end thereof and a base at a proximal end thereof, said tip carrier tube having a spiral groove and being rotatably mounted to said base;

a tip assembly mounted to the tip carrier tube by a tip coupler plug threaded to the tip carrier tube, the tip assembly including at least one movable tip element;

a tip element driver assembly including a user manipulatable tip element actuator, movably mounted tot he base at the proximal end of the body, and an axial driver assembly, movably mounted to the body, coupling the tip element actuator to at least the tip element, so that when the user manipulates the tip element actuator the tip element moves relative to the body; and a tip assembly rotator including a user manipulatable rotary actuator, movably mounted to the proximal end of the body, and a rotary driver, drivingly coupling the rotary actuator and the tip assembly, said rotary actuator also including a rotary actuated finger element slidably mounted to said base, said rotary actuated finger element having a cam pin slidably engaging said spiral groove so that linear movement of the rotary actuator finger element causes the cam pin to move along the spiral groove formed int he tip carrier tube thereby rotating the tip carrier tube and the tip assembly mounted thereto.

7. The instrument of claim 6 wherein the tip assembly is removably mounted to the tip carrier tube.

8. An endoscopic tissue manipulator comprising:

a body having distal and proximal ends with a longitudinal axis defined between the distal and proximal ends;

a tip assembly removably mounted to the body;

the tip assembly including first and second jaws, at lest the first jaw being movable relative to the second jaw between open and closed jaw positions;

user actuated means for moving at least the first jaw between the open and closed jaw positions;

the moving means including jaw actuating finger and thumb elements movably mounted to the body and positioned on opposite sides of the axis; and user actuated means, positioned between said jaw actuating finger and thrum elements and responsive to axial movement relative to said longitudinal body, for rotating the jaws about the axis.

9. An endoscopic surgical instrument comprising:

a body having distal and proximal ends and a longitudinal axis therebetween;

at least one movable tip element mounted to the distal end of the body for movement relative to the body;

user actuated moving means for moving the at least one tip element relative to the body wherein the moving means includes jaw actuating finger and thumb elements movably mounted to the body on opposite sides of the axis for movement towards and away from one another; and user actuated means for rotating the at least one tip element abut the axis.

10. The instrument of claim 9 further comprising a tip assembly removably mounted to the distal end of the body wherein the at least one movable tip element is part of sad tip assembly.

* * * * *